United States Patent [19]

Woodhouse

[11] 4,416,894
[45] Nov. 22, 1983

[54] ORGANIC COMPOUNDS

[75] Inventor: Christopher R. J. Woodhouse, London, England

[73] Assignee: Sandoz Ltd., Basel, Switzerland

[21] Appl. No.: 342,064

[22] Filed: Jan. 25, 1982

[30] Foreign Application Priority Data

Jan. 30, 1981 [GB] United Kingdom ............... 8102952

[51] Int. Cl.³ ................. A61K 31/415; A61K 31/435
[52] U.S. Cl. ................................. 424/273 R; 424/256
[58] Field of Search .................. 424/273 R, 258, 256; 260/326.1

[56] References Cited

U.S. PATENT DOCUMENTS 3,763,178 10/1973 Sulkowski ..................... 260/309.6
4,101,553 7/1978 Houlihan ......................... 260/288

Primary Examiner—Jerome D. Goldberg
Assistant Examiner—John W. Rollins
Attorney, Agent, or Firm—Gerald D. Sharkin; Robert S. Honor

[57] ABSTRACT

5-phenyl-5-hydroxy-2,3-dihydro-5H-imidazo [2,1-a]-isoindole derivatives for the treatment of urinary frequency, urgency and incontinence.

2 Claims, No Drawings

ORGANIC COMPOUNDS

This invention relates to compounds of formula I

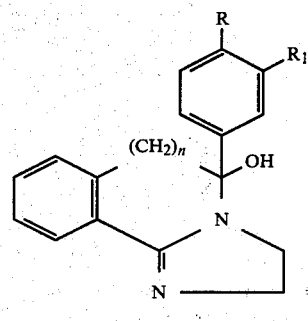

in which
n is 0 or 1 and
R and $R_1$ which may be the same or different, are hydrogen, fluorine or chlorine,
in free base form or in the form of pharmaceutically acceptable acid addition salts.

The compounds of formula I and processes for their production are known [for example J. Org. Chem. 33(7), 2874–2877 (1968)] as is their use as e.g. appetite suppressants. It is also known that the compounds of formula I may exist in various tautomeric forms, for example when in acid addition salt form. For the sake of simplicity, reference is herein made only to the form of formula I, but it is to be understood that the invention is not intended to be limited to any particular form of the compounds.

In accordance with the present invention compounds of formula I are useful in the treatment of urinary incontinence of various aetiology even in cases in which long-standing and severe symptoms had not responded to other treatments. A particularly preferred compound for use according to the invention is 5-(p-chlorophenyl)-5-hydroxy-2,3-dihydro-5H-imidazo [2,1-a]isoindole (Mazindol).

Clinical Trial

Patients and Methods

Thirty-six patients with urinary incontinence of various types were given Mazindol in doses of 1, 2 or 3 mg daily in single or divided dosage. They were warned that their appetite might be reduced and were asked to note its other effects.

The patients fell into several groups. The most significant were women with idiopathic detrusor instability and men with damaged external sphincters from surgery or trauma (Table). The remaining patients were a varied lot and included 7 who complained of frequency and urge incontinence but who had no demonstrable urodynamic abnormality ('sensory' frequency).

All of these patients were given Mazindol for very long-standing symptoms that had not responded to a wide range of more conventional treatments.

Results

Incontinence, frequency and urgency were completely or partly relieved in all but 10 of 36 patients (Table). The most striking responders were patients with idiopathic detrusor instability (7 of 10 cured), enuresis (4 of 4 cured) and sensory frequence (5 of 7 cured). Two women with neurological lesions did not respond.

Minor side-effects were quite common and in 4 patients light-headedness, insomnia, dry-mouth and depression were observed.

Table

Results of pilot study of Mazindol 1, 2 or 3 mg daily in urinary incontinence.

| Aetiology of incontinence | Total | Cured | Improved | No change |
|---|---|---|---|---|
| Sphincter damage* | 8 | 5 | | 3 |
| Idiopathic detrusor instability | 10 | 7 | 1 | 2+ |
| Sensory frequency | 7 | 5 | 1 | 1 |
| Adult enuretic | 4 | 4 | | |
| Stable stress | 2 | | 1 | 1 |
| Multiple sclerosis | 2 | | | 2 |
| Cauda equina lesion | 1 | | | 1 |
| Diabetic neuropathy | 1 | 1 | | |
| 2y to bladder Ca | 1 | 1 | | |
| Totals | 36 | 23 | 3 | 10 |

*5 following prostatectomy
1 following prostatectomy and urethroplasty
1 prostatic carcinoma
1 ruptured urethra followed by urethroplasty
+Incl. 1 child The present invention accordingly provides a pharmaceutical composition for the treatment of urinary frequency, urgency or incontinence comprising a compound of formula I, in free base or pharmaceutically acceptable acid addition salt form and a method of treating urinary frequency, urgency or incontinence which comprises administering to a subject in need of such treatment a compound of formula I in free base or pharmaceutically acceptable acid addition salt form.

The dosage of active agent to be administered will of course vary depending on the severity of the condition being treated and on the particular compound of formula I being employed.

However, an indicated suitable daily dosage is from 0.001 to 0.2 mg/kg of animal body weight giving for larger mammals a total daily dosage of from 0.1 to 20 mg preferably 0.1 to 5 mg suitably administered in doses of from 0.025 to 10 mg, two to four times daily, or in sustained release form. A preferred total daily dosage, for e.g. Mazindol is from 0.1 to 2 mg whereby dosages of up to 6 particularly 3 and 4 mg daily are also effective but may cause undesirable side effects.

The compounds of formula I may be employed in free base form or in the form of pharmaceutically acceptable acid addition salts, which salt forms have the same order of activity as the free base forms. Suitable acid addition salt forms include mineral acid salt forms, e.g. the hydrochloride, hydrobromide, sulphate or phosphate, and organic acid salt forms, e.g. the succinate, maleate, fumarate, acetate or p-toluenesulphonate.

The compounds may be administered in conventional pharmaceutical forms, in particular those already described in connection with administration for other indications e.g. appetite suppressant.

The preferred pharmaceutical compositions from the standpoint of ease of preparation and administration are integral solid unit dosage forms, e.g. tablets and capsules.

We claim:
1. A method of treating urinary frequency, urgency or incontinence which comprises orally administering to a patient in need of such treatment an effective amount of a compound of formula I

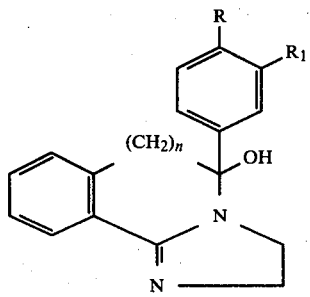

in which
n is 0 or 1 and
R and R₁ which may be the same or different, are hydrogen, fluorine or chlorine,
in free base form or in the form of a pharmaceutically acceptable acid addition salt.

2. A method as claimed in claim 1 wherein the compound employed is 5-(p-chlorophenyl)-5-hydroxy-2,3-dihydro-5H-imidazo [2,1-a] isoindole or a pharmaceutically acceptable acid addition salt thereof.

* * * * *